(12) United States Patent
Steinthorsson

(10) Patent No.: US 11,926,046 B2
(45) Date of Patent: Mar. 12, 2024

(54) TUNABLE STATIC BALANCER IN PARTICULAR FOR DEVICES WITH COMPLIANT MECHANISM

(71) Applicant: REON EHF., Reykjavik (IS)

(72) Inventor: Asthor Tryggvi Steinthorsson, Reykjavik (IS)

(73) Assignee: REON EHF., Reykjavik (IS)

( * ) Notice: Subject to any disclaimer, the term of this patent is extended or adjusted under 35 U.S.C. 154(b) by 729 days.

(21) Appl. No.: 16/764,508

(22) PCT Filed: Nov. 19, 2018

(86) PCT No.: PCT/IS2018/050012
§ 371 (c)(1),
(2) Date: May 15, 2020

(87) PCT Pub. No.: WO2019/097552
PCT Pub. Date: May 23, 2019

(65) Prior Publication Data
US 2020/0353632 A1 Nov. 12, 2020

(30) Foreign Application Priority Data

Nov. 17, 2017 (IS) .......................................... 050195

(51) Int. Cl.
*B25J 19/06* (2006.01)
*A61B 17/29* (2006.01)
(Continued)

(52) U.S. Cl.
CPC ............. *B25J 19/068* (2013.01); *A61B 17/29* (2013.01); *B25J 15/0028* (2013.01); *F16F 3/02* (2013.01);
(Continued)

(58) Field of Classification Search
CPC ..... B25J 19/068; B25J 15/0028; A61B 17/29; A61B 2017/2902; A61B 2017/2917;
(Continued)

(56) References Cited

U.S. PATENT DOCUMENTS 9,044,243 B2* 6/2015 Johnson ................. A61B 17/00
9,161,803 B2* 10/2015 Yates ................... H01M 50/531
(Continued)

FOREIGN PATENT DOCUMENTS

NL 2009200 1/2014
WO 03013374 A1 2/2003
(Continued)

OTHER PUBLICATIONS

International Search Report and Written Opinion dated Mar. 14, 2019 for corresponding International Application No. PCT/IS2018/050012.
(Continued)

Primary Examiner — Stephen A Vu
(74) Attorney, Agent, or Firm — TAROLLI, SUNDHEIM, COVELL & TUMMINO L.L.P.

(57) ABSTRACT

A tunable static balancer arrangement on a mechanic device, for adjustably compensating a positive force needed to actuate a moveable part of the device from a first position to a second position. The arrangement comprises a moveable actuation member for transferring movement from an input to said moveable part, the actuation member being moveable in a general axial direction, at least one first stiffness element that exerts in at least one position a negative force in the axial direction counteracting at least partially said positive force when the moveable part is moved from the first position to the second position, at least one adjustable second stiffness element, wherein said first stiffness element is connected on one end to said moveable actuation member, (Continued)

and on the opposite end to the adjustable second stiffness element, such that the first stiffness element exerts a positive force on the adjustable second stiffness element, and such that when stiffness of said adjustable second stiffness element is adjusted, the negative force of said first stiffness element in the axial direction is altered. Also provided is a compliant grasper comprising the tunable static balancer arrangement.

17 Claims, 7 Drawing Sheets

(51) Int. Cl.
  *B25J 15/00* (2006.01)
  *F16F 3/02* (2006.01)
(52) U.S. Cl.
  CPC ............. *A61B 2017/2902* (2013.01); *A61B 2017/2917* (2013.01); *A61B 2017/2937* (2013.01); *F16F 2228/066* (2013.01)
(58) Field of Classification Search
  CPC .... A61B 2017/2937; A61B 2017/2901; A61B 2017/2926; A61B 34/76; A61B 2090/034; F16F 3/02; F16F 3/023; F16F 2228/066; F16F 2228/063
  See application file for complete search history.

(56) References Cited

U.S. PATENT DOCUMENTS

| 2012/0215220 | A1  | 8/2012  | Manzo |
| 2015/0209059 | A1  | 7/2015  | Trees |
| 2015/0209573 | A1* | 7/2015  | Hibner ............... A61B 18/1442 606/48 |
| 2017/0296212 | A1* | 10/2017 | Ding .................... A61B 17/295 |
| 2018/0132925 | A1* | 5/2018  | Allen, IV ........... A61B 18/1445 |

FOREIGN PATENT DOCUMENTS

| WO | 03026519 A1   | 4/2003 |
| WO | 2012015301 A2 | 2/2012 |
| WO | 2013018934 A1 | 2/2013 |
| WO | 2016053863 A1 | 4/2016 |
| WO | 2017037532 A1 | 3/2017 |

OTHER PUBLICATIONS

Icelandic Search Report dated Feb. 26, 2018 for corresponding Application No. SE 2017 03044.
Stapel, A., et al. (2004). "Feasibility Study of a Fully Compliant Statically Balanced Laparoscopic Grasper." vol. 2: 28th Biennial Mechanisms and Robotics Conference, Parts A and B. doi:10.1115/detc2004-57242.

* cited by examiner (a)  (b)

TUNABLE STATIC BALANCER IN PARTICULAR FOR DEVICES WITH COMPLIANT MECHANISM

RELATED APPLICATIONS

The present application is a U.S. National Stage application under 35 USC 371 of PCT Application Serial No. PCT/IS2018/050012, filed on 19 Nov. 2018; which claims priority from IS Patent Application No. 050195, filed 17 Nov. 2017, the entirety of both of which are incorporated herein by reference.

FIELD

The invention relates to devices and mechanisms that apply static balancing for counteracting actuation forces, such as in particular in mechanical devices using compliant mechanism for actuation of movement.

INTRODUCTION

Compliant mechanisms in the context of mechanical engineering refer to flexible mechanisms that transfer an input force or displacement to another point through elastic body deformation. These may be monolithic (single-piece) or jointless structures.

Compliant mechanisms are being developed as alternatives to conventional hinge/joint-based movement in various devices, including surgical graspers, such as in particular laparoscopic graspers. Compliant graspers provide advantages such as in terms of compactness, no need for lubrication, ease of sterilization, etc. Compliant graspers are disclosed for example in Stapel A, Herder, J. L. *Feasibility Study of a Fully Compliant Statically Balanced Laparoscopic Grasper* Proceedings DETC'04 (DETC2004-57242).

A compliant mechanism such as a compliant grasper will typically have one particular resting position of the grasper jaws, which is maintained when no force is applied. This may be an open position, and then a force needs to be applied in order to move the jaws into a more open position or a closed position, and the applied force generally needs to be maintained to keep the grasper in the non-balanced position. This may cause fatigue in the hands of the surgeon. Another challenge in compliant mechanisms such as compliant graspers and other devices where accurate force transfer is of concern, is lack of intuitive force feedback, since the force transmission acts through elastic energy in the compliant parts. This means that the needed actuation force on the handle of a grasper is often not in an intuitive relation to the force being applied by the jaws. For example, when a delicate object is being gripped and held by the grasper, the force applied by the grasper jaws must be limited and accurately applied in order not the damage the object. This can be difficult when the force applied by the jaws is not the same as the actuation force applied on the grasper handle, and if the relationship between the two is not linearly intuitive.

To affect the relationship between the force applied to the handle and the force applied by the jaws, variants have been introduced with means for force balancing, such as by introducing a static balancer.

One way of addressing this is to attempt to statically balance the elastic forces needed to change the compliant mechanism by introducing force compensation, such as by spring force compensation.

NL 2009202 discloses a grasper embodied with a bi-stable element and grasper legs (grasper jaws) which legs have a stable first position and a stable second position, and wherein converting between the first position and the second position and vice versa is supported by the bi-stable element. The bi-stable element is essentially in the form of a leaf spring connected to a longitudinal member that is used to convey force and movement to the grasper legs, the exact position of the bi-stable element connection on the longitudinal member can be adjusted by means of fixing means (nuts) that are moveable along the member. The bi-stable element is arranged to exert negative stiffness towards movement of the grasper legs, thus compensating for positive stiffness of the grasper legs.

WO 03/026519 discloses a grasper (gripping tongs) with a handle and jaws connected thereto by an operating rod. The gripper mechanism has the feature that it has a positive spring characteristic. The grasper also comprises a compensating mechanism that has the feature that it has a negative spring characteristic. The steepness of the negative spring characteristic is adjustable. The specific embodiments disclosed employ one or more leaf springs connected to the operating rod and perpendicular to it, where the ends of the leaf springs are connected to respective tensioning elements, the distance between which can be adjusted by means of adjusting bolts.

NL 2009200 discloses a grasper embodied with a bi-stable element and grasper legs, which legs have a stable first position and a stable second position, and converting between the two is supported by the bi-stable element, which is arranged with a negative stiffness that is higher in magnitude and counteracts the positive stiffness of the grasper legs. The actuation part of the grasper may be spring-loaded to provide additional positive stiffness to the positive stiffness of the grasper legs in order to substantially match he negative stiffness of the bi-stable element when the legs convert between the first position and the second position.

It still remains a challenge to accurately adjust force compensation in statically balanced devices and to apply force compensation over a movement range.

SUMMARY

The present invention provides a tuner/tuning mechanism for static balancers that can be applied in, but are not limited to, compliant graspers. Most generally, a static balancer arranged with a tuner of the invention, comprises at least a member for storing potential energy that is arranged to compensate an actuation force that is needed to actuate a device.

One aspect of the invention provides a tunable static balancer arrangement on a mechanic device, for adjustably compensating a positive force needed to actuate a moveable part of the device from a first position to a second position, comprising: a moveable actuation member for transferring movement from an input to said moveable part, said actuation member being moveable in a general axial direction of the actuation member; at least one first stiffness element that exerts a negative force in the axial direction counteracting said positive force when the moveable actuation member is moved in order to move the moveable part from the first position to the second position; an adjustable second stiffness element, wherein said first stiffness element is connected on one end to said moveable part, and on the opposite end to the adjustable second stiffness element, wherein the first element exerts a positive force on the adjustable second stiffness element, such that when stiffness of said adjustable stiffness element is adjusted, the negative force of said bi-stable element is altered.

The mechanic device can in general be any mechanic device with a moveable part which benefits from a static balancer, and in particular devices where it can be a challenge to readily prepare and install beforehand the static balancer such that its balancing force is accurately tuned and where a tunable static balancer therefore is beneficial.

As appears from the disclosure herein the static balancer of the invention suitable but not limited to a compliant grasper. Other compliant devices and compliant arrangements can also benefit from the tunable static balancer arrangement of the present invention, such as but not limited to prosthetic devices, industrial robots, etc.

Accordingly, the invention provides in another aspect a compliant grasper comprising at least two jaws that can be moved towards and away from each other, to hold and release an object in between the jaws, wherein the jaws are moved through a compliant bending mechanism according to the invention; a handle portion for actuating the compliant bending mechanism; and a static balancer connected to the compliant bending mechanism, wherein the static balancer comprises at least one first stiffness element for counteracting the actuation force of the compliant bending mechanism, wherein the at least one first stiffness element is connected to at least one second stiffness element with adjustable stiffness, so that its stiffness can be tuned to thereby adjust the force compensation of the static balancer.

The above features along with additional details of the invention are described further in the examples below, which are intended to further illustrate the invention but are not intended to limit its scope in any way.

BRIEF DESCRIPTION OF THE DRAWINGS

The skilled person will understand that the drawings, described below, are for illustration purposes only. The drawings are not intended to limit the scope of the present teachings in any way.

DESCRIPTION OF VARIOUS EMBODIMENTS

In the following, exemplary embodiments of the invention will be described, referring to the figures. These examples are provided to provide further understanding of the invention, without limiting its scope.

The tunable static balancer of the invention is generally suitable and can readily be customised to a range of different devices and applications, where such tunable function of a static balancer is desired. This invention describes in detail embodiments of the static balancer implemented in a laparoscopic compliant grasper, and such grasper is also a part of this invention. The general concept provided herein of a static balancer is however not limited to such embodiments nor is it limited to compliant mechanisms. The tunable static balancer is however useful in various devices that apply a compliant mechanism. The term "compliant mechanism" is as such well known to the skilled person and is already briefly described in the Introduction section of this disclosure.

Figure 1:
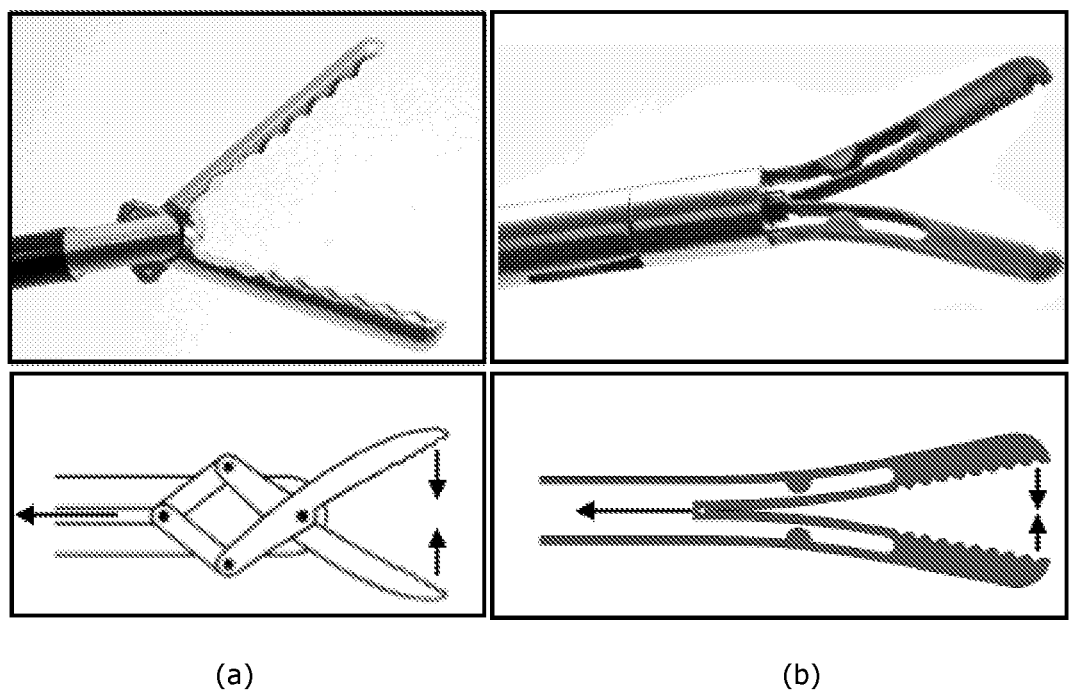
FIG. 1 shows a general comparison between the jaw part of a conventional hinge-based grasper and a compliant grasper.
Figure 2:
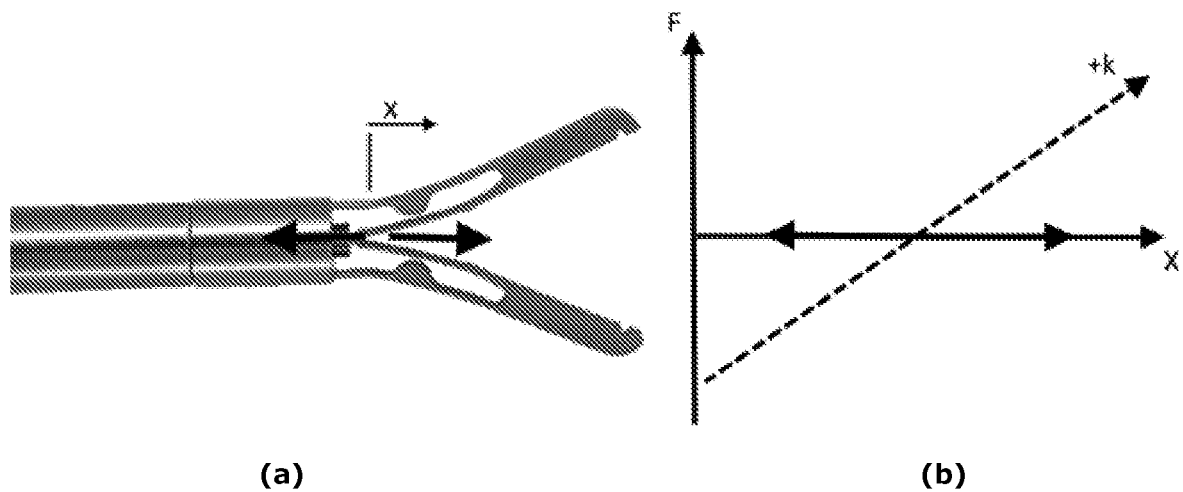
FIG. 2 illustrates the force needed to actuate the movement of a compliant mechanism such as the jaws of a compliant grasper.

As a non-limiting illustration and explanation of the general concepts involved in the present invention, FIG. 1 shows a general comparison between (a) a conventional grasper with a hinge-based movement mechanism, and (b) a compliant grasper. FIG. 2 illustrates the general force needed for bending the compliant parts that actuate the movement of the grasper jaws. Typically there exists a resting equilibrium position where the compliant parts are without tension, in a compliant grasper the equilibrium (resting) position of the compliant bending parts is typically either when the grasper is closed or half-open, The diagram in panel (b) of FIG. 2 indicates that the equilibrium position is a half-open position of the grasper jaws. To move away from the equilibrium a force is needed, which can be generally illustrated as k*x (the force can be approximated as linear over a limited range, as the compliant bending parts can be generally described with linear elastic spring forces).

Figure 3:
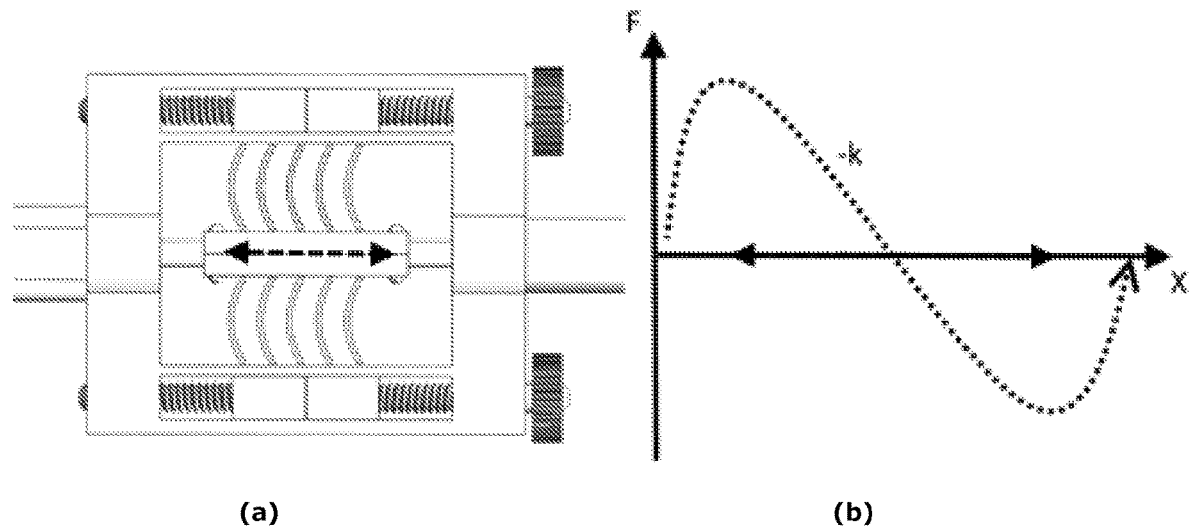
FIG. 3 shows the axial force effected by a bi-stable static balancer.

FIG. 3 shows the general effect of introducing a static balancer, i.e. a mechanism that would counteract the force k*x. In the perfect situation the counteracting force is $-k*X$, i.e. it balances out the actuation force k*X over the movement range. This would mean that a user using such balanced compliant grasper does not have to apply any force to overcome an actuation force, instead the grasper behaves more like regular friction-free hinged forceps, which in turn means that any resistance that extends from the grasper jaws to the handle corresponds to actual resistance of the object being grasped by the jaws. Thus, a force applied to the handle is transferred to the jaws and the same force is applied to an object held by the grasper. In practice however, a bi-stable static balancer can balance out the force k*x over a certain linear region.

Figure 4:
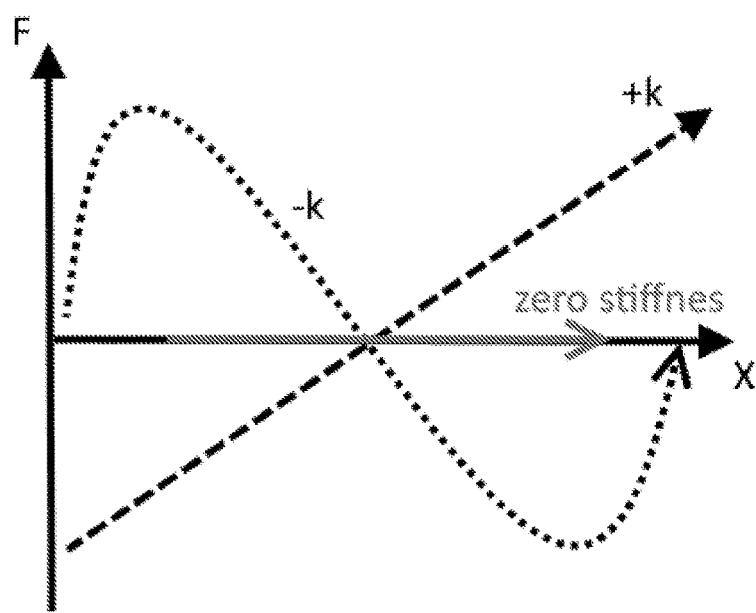
FIG. 4 shows the combination of an actuation force a compliant mechanism and a counteracting static balancer.

FIG. 4 shows a diagram summing together the force of a compliant grasper when the static balancer is a bi-stable configuration.

A challenge when introducing the counteracting balancer in practice is how to accurately adjust the force to obtain optimal balancing. The present invention provides a new and improved tuning mechanism for this purpose. In the tuner of the present invention a first stiffness element exerts a negative force counteracting at least partially the positive actuation force of the device in question, and the first stiffness element is connected to an adjustable second stiffness element, such that the first stiffness element exerts a positive force on the adjustable second stiffness element. It follows that the second stiffness element is able to absorb at least a portion of the positive force exerted by the first element, and the degree of this absorption is altered with adjustment of the stiffness of the second element. This in turn means that when the stiffness of the second element is adjusted, the negative force that the first element exerts in the axial direction counteracting the actuation force, is correspondingly adjusted.

In the definition herein of the static balancer it is generally assumed that the moveable part needs to be moved from a first position to a second position and that to actuate this movement a positive force is required. The tunable static balancer arrangement generally comprises a moveable actuation member which has an axial direction and is typically an elongated member. The actuation member is moveable in the general axial direction.

The at least one first stiffness element in some embodiments comprises at least one first spring element, such as for example a leaf spring, and in one embodiment a plurality of leaf springs.

In some embodiments the mentioned first stiffness element comprises a stiffness element in a bi-stable configuration. The term "bi-stable configuration" is well known in the art and refers generally to a system that has two stable equilibrium states. These two equilibrium states need not be symmetric with respect to stored energy. The bi-stable system will generally have a non-stable intermediate state that the system has to pass through in order to change from one equilibrium state to the other.

The mentioned at least one second stiffness element comprises in certain embodiments at least one second spring element, which in certain embodiments is a spring element which can be defined as a leaf spring. In certain embodiments the stiffness of the second stiffness element is adjusted by adjusting its length. This is done in some embodiments with moveable and/or adjustable clamps that restrict and shorten the effective length of a central more flexible portion of the second stiffness element.

In useful embodiments the at least one first stiffness element comprises at least one pair of oppositely arranged first stiffness elements, and the at least one adjustable second stiffness element comprises at least one pair of oppositely arranged second stiffness elements. In this embodiment the respective proximal ends of said first stiffness elements are connected to the mentioned actuation member, and the distal ends of the first stiffness elements each connects to at least one respective second stiffness element. Thus a symmetric arrangement is provided, examples of such embodiments are shown in FIGS. 5-9.

In certain embodiments, the at least one first stiffness element can have one or both of its connecting ends in a pinned configuration. The term "pinned configuration" as used herein refers generally to the term "pinned" as used in the context of structural boundary conditions, thus "pinned" in this context means that the respective connecting point is essentially a freely rotating point. In contrast, a "clamped configuration" or clamped boundary condition, would indicate that the respective end is rigidly fixed to its connecting support and thus angular movement of the element around the connecting point requires bending of the element (and thus will need to overcome an elastic force of the element due to that bending). In some embodiments the proximal connection of the at least one first stiffness element, that is, the connection to the moveable actuation member, has a pinned configuration, whereas the distal connection, the connection of the first stiffness element to the second stiffness element, has a clamped configuration. In another embodiment, both the proximal and the distal connection of the at least one first stiffness element has a clamped configuration. The embodiment exemplified in FIGS. 5-9 is an illustration of an arrangement with both the distal and proximal end connections of the first stiffness elements being in a pinned configuration. In yet another embodiment the proximal connection of the first stiffness element(s) has a clamped configuration whereas the distal connection of the first stiffness element has a pinned configuration.

A pinned configuration of the first stiffness element is in some embodiments arranged by having a hole through the end of the element, or a hook, that fits on to a pin arranged on the connecting part, or vice versa, that is the first stiffness element can have a pin or protrusion that rotates in a mating hole on the connecting part. In another embodiment the pinned configuration is arranged by having the end of the element rest in a suitably shaped seat in the connecting part, in which seat the element end has sufficient freedom to move to allow sufficient angular movement of the element. This can also be referred to as a knife joint, and accordingly, in the present invention one or both ends can be connected through a knife joint. In the embodiment depicted in FIGS. 5-9, the first stiffness element is connected on both ends via knife joints, as is most clearly seen in FIGS. 8 and 9.

As mentioned above, another aspect of the invention sets forth a compliant grasper which comprises a tunable static balancer according to the present invention. The compliant grasper can advantageously be configured with, but is not limited to, a tunable static balancer based on a bi-stable element, where the at least one first stiffness element comprises at least one bi-stable element, such as described above. The tunable static balancer comprised in the grasper of the invention can essentially have any one or more of the above features that have been described generally for the tunable static balancer of the invention.

Turning to illustrations and examples of specific embodiments, FIGS. 5-9 show an embodiment of the invention, specifically a symmetric tunable balancer with series of parallel leaf springs 1 arranged as the first stiffness elements. The leaf springs 1 are arranged between an axial moveable actuation member 3, which has fastened on it a sleeve 4 that moves with the actuation member and has seats 9 for accommodating the proximal ends 7 of the leaf springs 1. The distal ends 8 of the leaf springs 1 are placed in seats 10 arranged in the respective two second stiffness elements 2, which are configured as parts of a frame 16 that holds the balancer in place. The stiffness of stiffness elements 2 is adjusted with adjustment means which in this embodiment comprise bidirectional screws 12 with screw heads 13. By turning the screws, adjustment blocks 11 are either moved closer together or further apart, changing the ratio between the length of distal rigid portions 14 of the second stiffness element and a central flexible portion 15. In this embodiment, the adjustable length of the central flexible portion controls the degree of stiffness of the second stiffness element. As seen, the static balancer in this embodiment is a symmetric balancer, with two symmetrically arranged sets of leaf springs 1,1' as the first stiffness elements, and two symmetrically arranged second stiffness elements 2,2'. Each set of leaf springs is connected to a respective second stiffness element.

Figure 6:
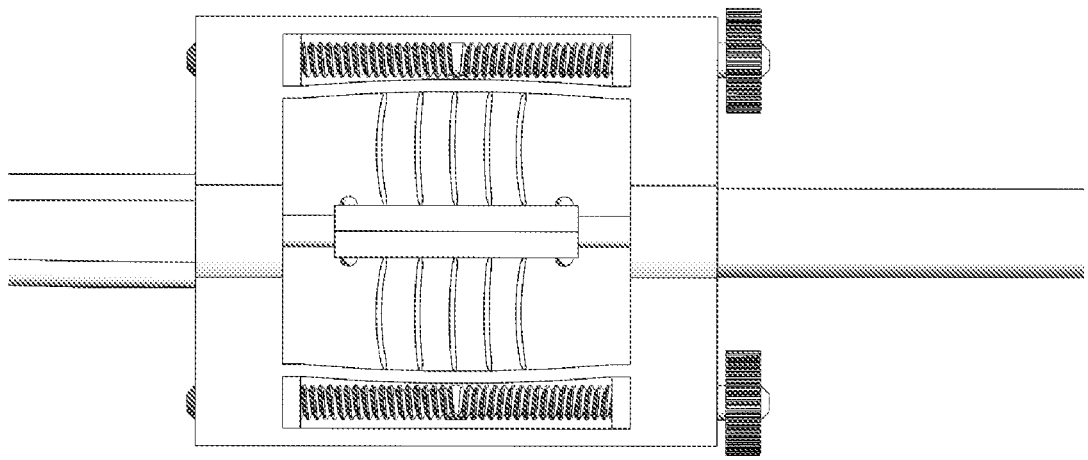
FIG. 6 shows the tunable balancer of FIG. 5, where the actuation member and leaf springs are in a central position.
Figure 7:
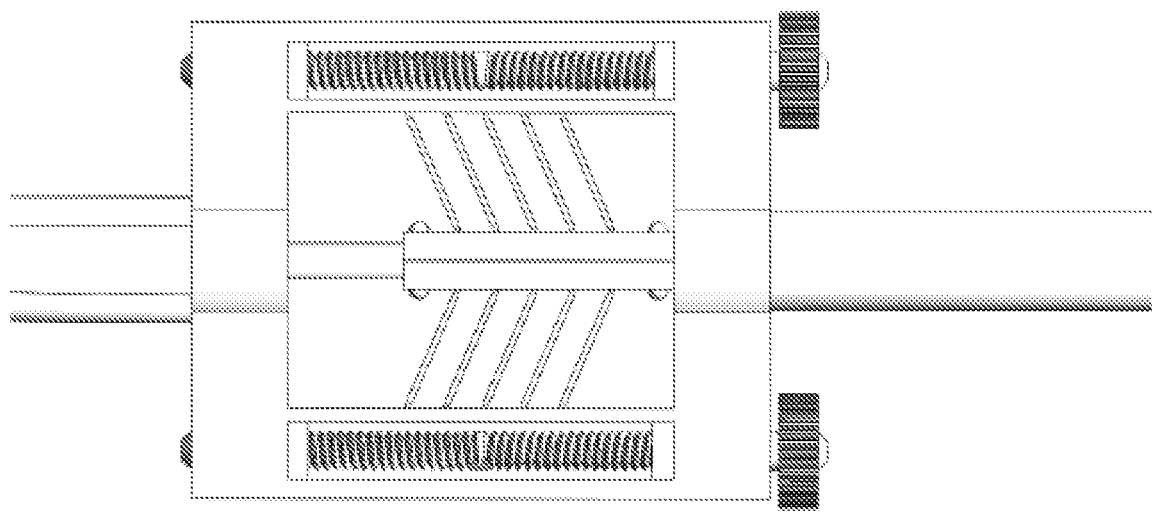
FIG. 7 shows the tunable balancer of FIG. 5, where the actuation member and leaf springs are in a right-most position.
Figure 8:
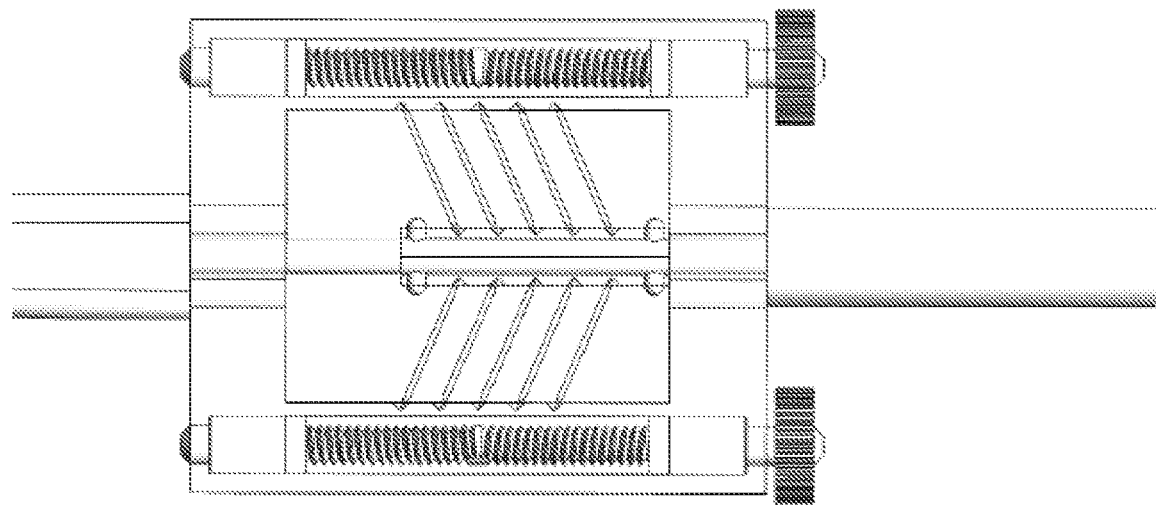
FIG. 8 shows a transparent view of the tunable balancer of FIGS. 5-7.

In the embodiment in FIGS. 5-8, the first stiffness elements are connected on each end with a pinned arrangement (also referred to as knife joints, as discussed above), by having each leaf spring shaped with pointed ends that sit in suitably shaped receiving seats, as shown more clearly in FIG. 8, where all parts are shown in transparent mode.

Figure 5:
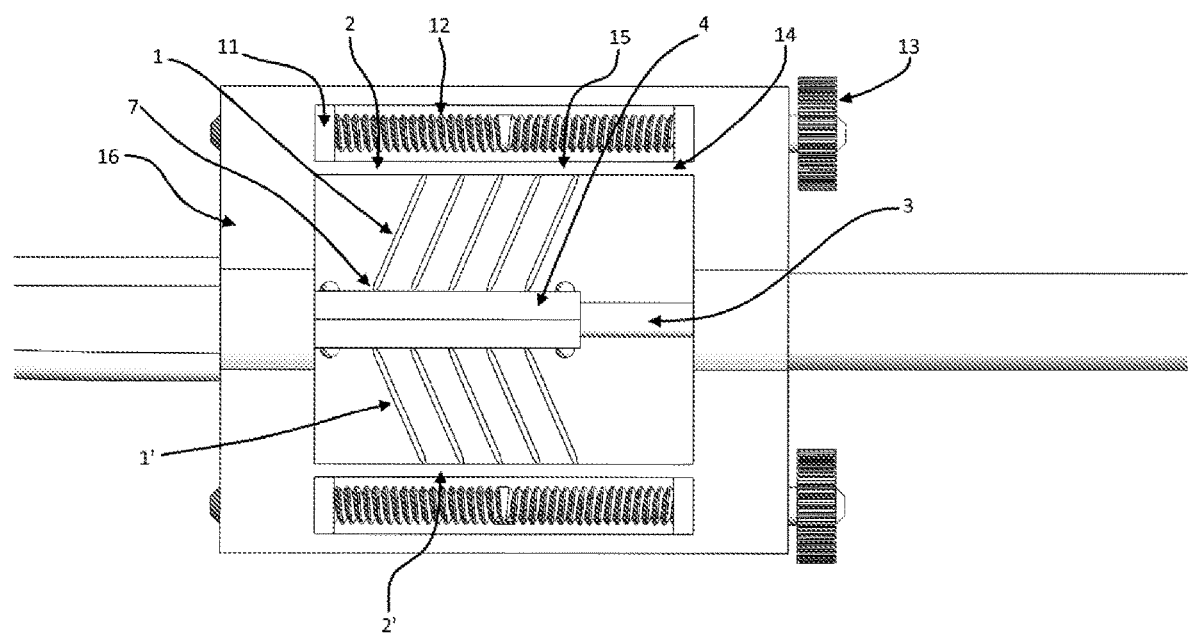
FIG. 5 shows an embodiment of a symmetric tunable balancer.

FIG. 5 shows the tuner as the moveable actuation member 3 is in its left-most position, where the fist stiffness element would typically but not necessarily be in a fully relaxed position where they do not exert any force in the axial direction. In FIG. 6, the member is in a central position, and it is seen how the first stiffness elements exert a force on the second stiffness elements that bend as a result, and thus absorb a portion of the spring force of the first stiffness elements. This mid-position corresponds to the central position in the general diagram depicted in FIG. 4 where the force value on the Y-axis (the axial force exerted by the static balancer) is at 0. In FIG. 7 the actuation member 3 is positioned in its right-most position and then the first stiffness elements have again been relaxed.

Figure 9:
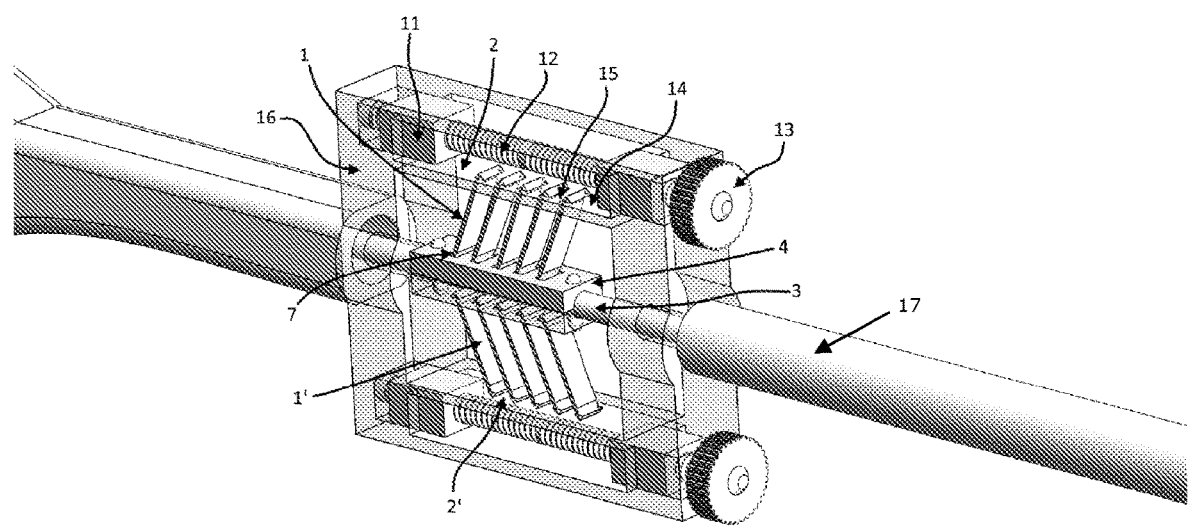
FIG. 9 shows a panoramic transparent view of the tunable grasper of FIGS. 5-8.

FIG. 9 shows a transparent panoramic view of the tuner described above. It is seen that in this embodiment the second stiffness elements are made from the same continuous piece of material as the frame 16. In other embodiments the second stiffness elements are made from separate pieces and the frame is shaped suitably to accommodate the second stiffness elements.

Figure 10:
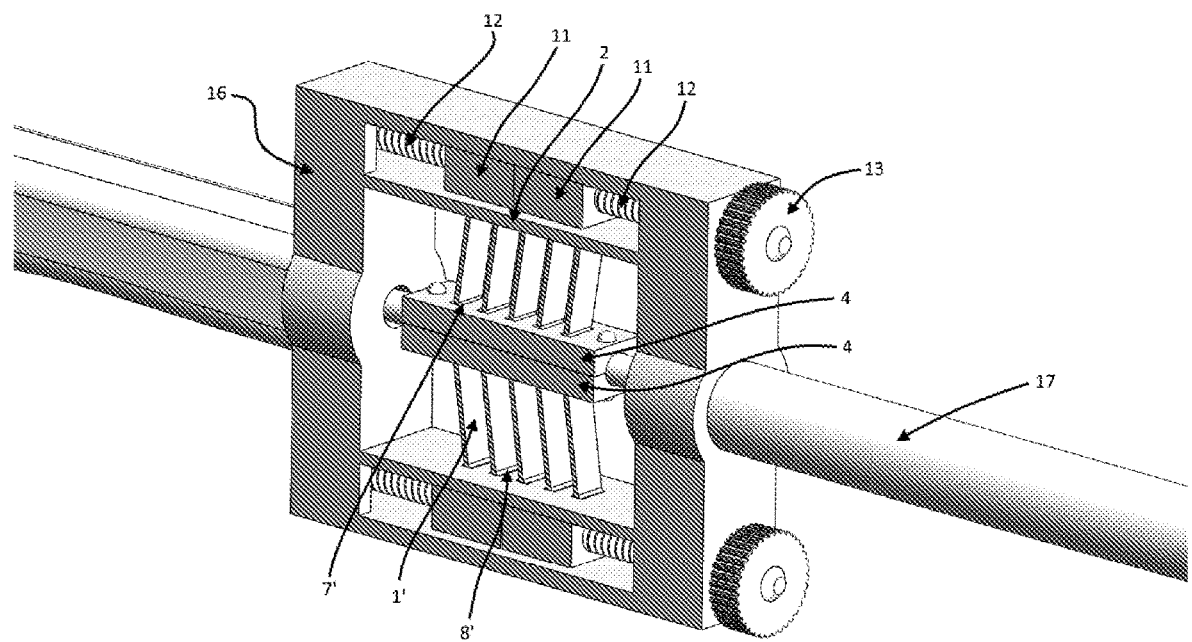
FIG. 10 shows a tunable balancer with first stiffness elements distally fastened to second stiffness elements with clamped arrangement.

FIG. 10 shows another embodiment of the adjustable tuner where the first stiffness elements 1 are fastened on their distal end 8,8' with a clamped arrangement (the distal end being the end adjoining the second stiffness element) and on the proximal ends 7,7' with pinned (knife-joint) arrangement as generally described above. The clamped configuration of the distal ends can for example be provided by soldering, gluing, or machining the first elements from the same block as the second stiffness element (which may or may not be a continuous part of the same material block as the frame 16). In other embodiments of clamped arrangement the ends of the first stiffness elements are positioned in snugly fitting grooves and/or fastened with fastening means such as screws.

In FIG. 10 the adjustment blocks 11 are shown positioned fully together, thereby maximising the stiffness of the second stiffness element 2, which in this position has no central flexible portion 15 remaining. In FIG. 9 these blocks are shown in a position far apart which means that the central flexible portion 15 of the second stiffness element 2 is extended.

Figure 11:
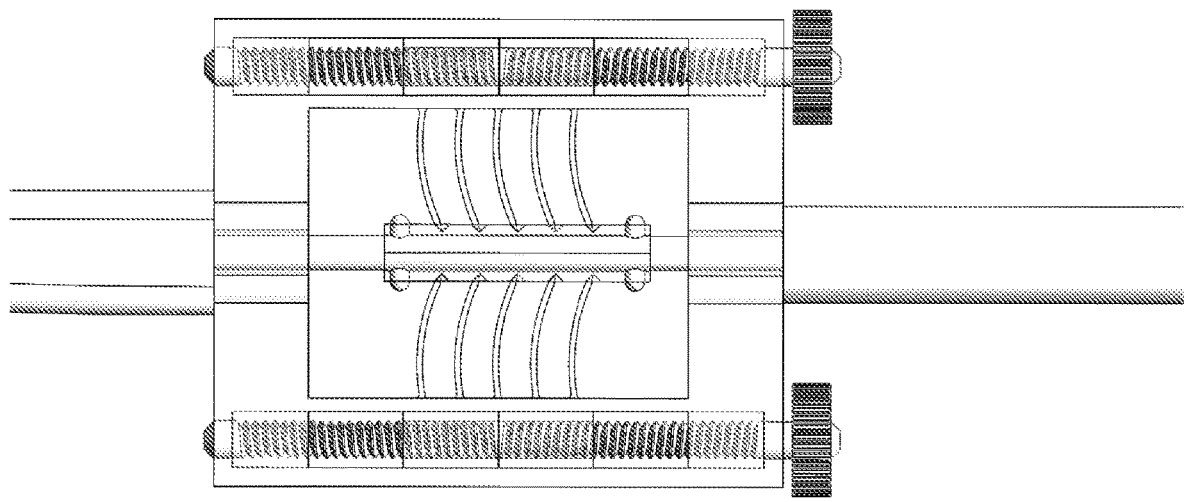
FIG. 11 shows a transparent view of the tunable balancer in FIG. 10.

FIG. 11 shows a transparent view of the same embodiment as in FIG. 10.

Figure 12:
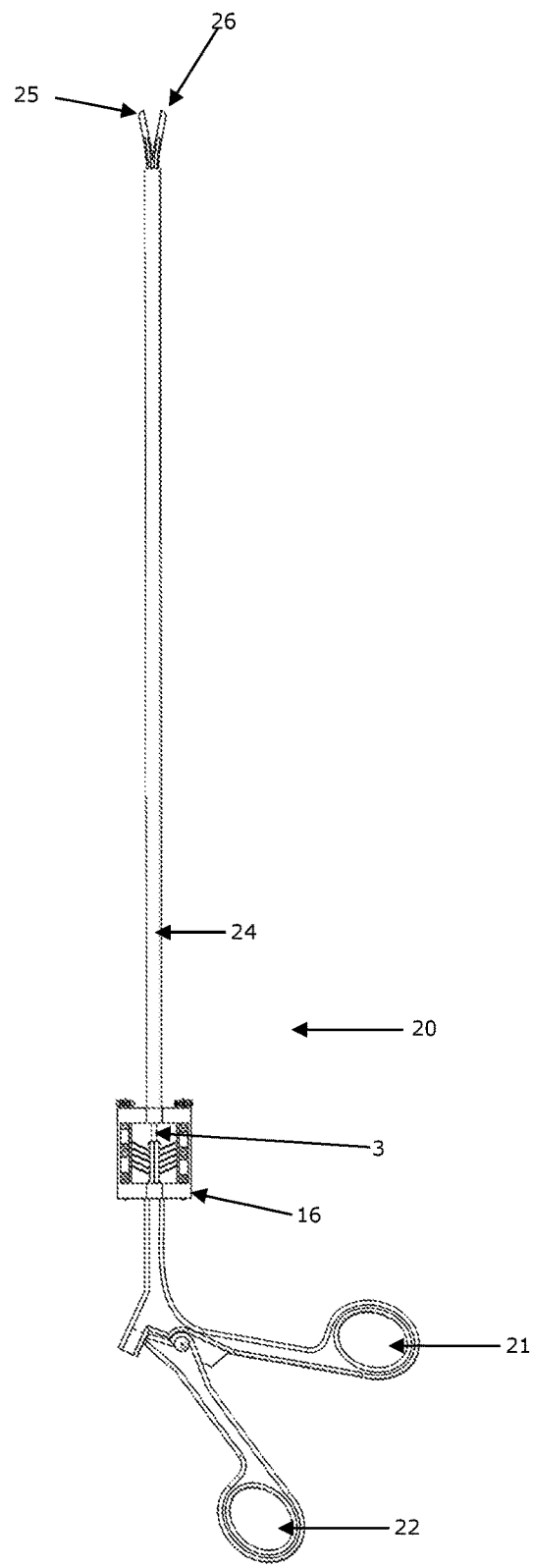
FIG. 12 shows a compliant grasper with associated tunable static balancer.

As has been described above, a tunable balancer of the invention, such as the embodiment described above, is suitable for balancing forces in a compliant grasper. An example of a balanced compliant grasper according to the invention is depicted in FIG. 12. In a grasper of the invention, the balancer is typically positioned such that the mid-position where the fist stiffness elements exert only a vertical force and no horizontal force (force in the axial direction) corresponds to the resting position of the compliant mechanism.

The grasper 20 comprises a handle for actuating the compliant bending mechanism, comprising at least a supported handle element 21 and a movable handle element 22.

The term "supported" in this context is used as is customary in the field of compliant mechanics, referring to a fixed point of reference. The grasper further comprises an elongated mechanism 24 for transferring movement actuation from the handle elements 21,22 to the jaws 25,26 and this elongated mechanism has an associated tunable balancer as described above. The tunable balancer is associated with an axial moveable actuation member 3, which connects one of the handle elements 21 or 22 to a connecting point of a moveable part of the compliant jaw mechanism 25,26, thus moving the handle element transfers movement to the grasper jaws and the force that is needed is counteracted by a linear force from the tunable balancer. Typically and as shown herein, the moveable member 3 is within a fixed sleeve 17 onto which the frame 16 of the tunable balancer is connected.

In one embodiment the elongated mechanism comprises an elongated support member connecting the supported handle element 22 and a supported connecting point 21 (or points) of the jaws, and an elongated actuation rod connecting the movable handle element and a moveable connecting point 20 of the jaws, wherein the elongated actuation rod comprises said inner rod of the compliant mechanism. The elongated support member preferably comprises or is fixedly adjoined to the outer fixed sleeve 17 of the moveable actuation member. The outer fixed sleeve is preferably in a fixed arrangement with the frame 16.

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components.

The present invention also covers the exact terms, features, values and ranges etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

The term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

It will be appreciated that variations to the foregoing embodiments of the invention can be made while still falling within the scope of the invention can be made while still falling within scope of the invention. Features disclosed in the specification, unless stated otherwise, can be replaced by alternative features serving the same, equivalent or similar purpose. Thus, unless stated otherwise, each feature disclosed represents one example of a generic series of equivalent or similar features.

Use of exemplary language, such as "for instance", "such as", "for example" and the like, is merely intended to better illustrate the invention and does not indicate a limitation on the scope of the invention unless so claimed. Any steps described in the specification may be performed in any order or simultaneously, unless the context clearly indicates otherwise.

All of the features and/or steps disclosed in the specification can be combined in any combination, except for combinations where at least some of the features and/or steps are mutually exclusive. In particular, preferred features of the invention are applicable to all aspects of the invention and may be used in any combination.

The invention claimed is:

1. A tunable static balancer arrangement on a mechanic device, for adjustably compensating a positive force needed to actuate a moveable part of the device from a first position to a second position, comprising:
   a moveable actuation member for transferring movement from an input to said moveable part, said actuation member being moveable in a general axial direction of the actuation member,
      at least one pair of oppositely arranged first stiffness elements that exert in at least one position a negative force in the axial direction counteracting at least partially said positive force when the moveable part is moved from the first position to the second position,
      at least one pair of oppositely arranged adjustable second stiffness elements, wherein proximal ends of said first stiffness elements are connected to said moveable actuation member which is connected to the moveable part, and opposite distal ends of the first stiffness elements connect to at least one of said pair of adjustable second stiffness elements, such that the first stiffness element exerts a positive force on the adjustable second stiffness element,
      such that when stiffness of said adjustable second stiffness element is adjusted, the negative force of said first stiffness element in the axial direction is altered.

2. The tunable static balancer arrangement of claim 1, wherein said at least one first stiffness element comprises a stiffness element in a bi-stable configuration.

3. The tunable static balancer arrangement of claim 1, wherein said at least one first stiffness element comprises at least one first spring element.

4. The tunable static balancer arrangement of claim 3, wherein said at least one first stiffness element comprises a plurality of leaf springs.

5. The tunable static balancer arrangement of claim 1, wherein said adjustable second stiffness element comprises at least one second spring element.

6. The tunable static balancer arrangement of claim 5, wherein said adjustable second stiffness element comprises a leaf spring.

7. The tunable static balancer of claim 1, wherein the stiffness of said adjustable second stiffness element is adjusted by adjusting its length.

8. The tunable static balancer of claim 1, wherein the mechanic device comprises a compliant mechanism for moving the moveable part of the device, and wherein said positive force is at least in part due to compliant movement of the compliant mechanism.

9. The tunable static balancer of claim 1, wherein one or both connecting ends of the at least one first stiffness element has a pinned configuration.

10. The tunable static balancer of claim 1, wherein said mechanic device is a compliant grasper.

11. A compliant grasper comprising
   at least two jaws that can be moved towards and away from each other, to hold and release an object in between the jaws, wherein the jaws are moved through a compliant bending mechanism,
   a handle portion for actuating the compliant bending mechanism,
   a moveable actuation member for transferring movement from said handle portion to said compliant bending mechanism, and
   a static balancer connected to the compliant bending mechanism,
   the static balancer comprising
   at least one pair of oppositely arranged first stiffness elements,
   at least one pair of oppositely arranged adjustable second stiffness elements,
   wherein said first stiffness element exerts a negative force in an axial direction for counteracting at least partially a positive actuation force of the compliant bending mechanism,
   wherein said first stiffness elements are connected on their proximal ends to said moveable actuation member, and on their distal end to one of said adjustable second stiffness element, and wherein one or both said ends of the at each least one first stiffness element has a pinned configuration, such that said first stiffness elements exert a positive force on the adjustable second stiffness elements and said adjustable second stiffness elements are able to absorb at least a portion of said positive force,
   wherein when stiffness of the adjustable second stiffness elements is adjusted the negative force of said first stiffness elements in the axial direction is altered.

12. The compliant grasper of claim 11, wherein said at least one first stiffness element comprises at least one bi-stable element.

13. The compliant grasper of claim 11, wherein said at least one first stiffness element comprises one or a plurality of leaf springs.

14. The compliant grasper of claim 11, wherein said at least one second stiffness element comprises a spring element, and wherein tuning said second stiffness element comprises stretching or loosening tension applied to one or both ends of said second stiffness element.

15. The compliant grasper of claim 11, wherein the stiffness of said adjustable second stiffness element is adjusted by adjusting its length.

16. The compliant grasper of claim 11, wherein said at least one first stiffness element comprises at least one bi-stable spring element.

17. A tunable static balancer arrangement on a mechanic device, for adjustably compensating a positive force needed to actuate a moveable part of the device from a first position to a second position, comprising:
   a moveable actuation member for transferring movement from an input to said moveable part, said actuation member being moveable in a general axial direction of the actuation member,
      at least one first stiffness element that exerts in at least one position a negative force in the axial direction counteracting at least partially said positive force when the moveable part is moved from the first position to the second position,
      at least one adjustable second stiffness element,
      wherein said first stiffness element is connected on one end to said moveable actuation member, and on an opposite end to the adjustable second stiffness element, such that the first stiffness element exerts a positive force on the adjustable second stiffness element, wherein one or both said ends of the at each least one first stiffness element has a pinned configuration,
      such that when stiffness of said adjustable second stiffness element is adjusted, the negative force of said first stiffness element in the axial direction is altered.

* * * * *